United States Patent [19]

Zardi et al.

[11] Patent Number: 5,135,722
[45] Date of Patent: Aug. 4, 1992

[54] CONVERTERS FOR HETEROGENEOUS CATALYTIC SYNTHESIS, PARTICULARLY FOR AMMONIA AND METHANOL, UNDER PRESSURE

[75] Inventors: Umberto Zardi, Breganzona; Giorgio Pagani, Lugano, both of Switzerland

[73] Assignee: Ammonia Casale S.A., Switzerland

[21] Appl. No.: 288,484

[22] Filed: Dec. 22, 1988

[30] Foreign Application Priority Data

Dec. 24, 1987 [CH] Switzerland .................. 05057/87

[51] Int. Cl.$^5$ .................. B01J 8/04; C01C 1/04
[52] U.S. Cl. .................. 422/148; 422/192; 422/198
[58] Field of Search ............... 422/148, 191, 192, 221, 422/239, 311, 198

[56] References Cited

U.S. PATENT DOCUMENTS

| | | | |
|---|---|---|---|
| 4,372,920 | 2/1983 | Zardi | 422/148 |
| 4,405,562 | 9/1983 | Zardi et al | 422/148 |
| 4,769,220 | 9/1988 | Zardi | 422/148 |

*Primary Examiner*—Joye L. Woodard
*Attorney, Agent, or Firm*—Ostrolenk, Faber, Gerb & Soffen

[57] ABSTRACT

A converter for heterogeneous catalytic synthesis under pressure, consisting of an external shell in a single piece and inside this of at least a cartridge containing a catalyst arranged in one or more beds contained in catalyst-carrying baskets. An external wall of these baskets is provided with means that protrude from the closed bottom and are coupled, in order to be supported, with means protruding from the internal continuous face which extends substantially along the entire axial height of the converter and is the nearest to the internal wall of the baskets. An unflanged labyrinth seal is located between two centrally located heat exchangers contained within the converter.

For reactions at high pressures, the wall holding the protruding support rings at the bottom of the baskets is a cartridge wall in a single piece that extends substantially along the whole shell and forms with this an airspace.

For reactions at low pressures, the support rings of the basket bottoms protrude from the internal surface of the shell. At least one of the catalytic beds supported by the baskets or elementary cartridges is centrally crossed by an indirect heat exchanger.

5 Claims, 6 Drawing Sheets

CONVERTERS FOR HETEROGENEOUS CATALYTIC SYNTHESIS, PARTICULARLY FOR AMMONIA AND METHANOL, UNDER PRESSURE

BACKGROUND OF THE INVENTION

1. Field of the Invention:

This invention relates to a converter for heterogeneous catalytic synthesis under pressure, particularly for the catalystic synthesis of ammonia and menthanol, consisting of an external shell in a single piece and, inside of this, of a cartridge containing catalyst of granule type and various characteristics arranged in one or more beds contained in modular baskets.

2. Description of the Related Art:

It is known that in this type of converters it is important to control the gas temperature at the inlet of the catalytic beds, such a control being preferably obtained in the converters with a higher yield by means of indirect cooling with the use of exchangers.

In converters of radial or axial-radial type already described in numerous patents of the Applicant (see, for example, the Swiss Patent No. 643752), the exchangers used for the control of the gas temperature are generally located in the central part of the catalytic beds, coaxial to the length of the converter itself.

The use of exchangers in converters with various beds (at least two), even if on one side they present the advantage of increasing the functioning yield with respect to the cooling systems between the beds obtained by means of fresh gas "quench", involves, on the other hand, notable constructive complications which render the access to single catalytic beds quite difficult in the catalyst installation and removal phases.

In Swiss Patent 643752, a first simplication was proposed wherein modular cartridges are superposed, each one containing a catalytic bed and, in at least one part of the bed, an exchanger is arranged coaxially with the converter axis.

According to that patent (see FIG. 8 of the text), each modular cartridge incorporated: a) a cylindrical solid external wall that constitutes a section of the external wall of the airspace forming cartridge with the internal wall of the external shell of the converter; b) an external cylindrical wall permeable to gas that constitutes the external distribution gas wall in the catalytic bed and of catalyst container, c) a cylindrical external wall permeable to gas that constitutes the internal gas distribution wall in the catalytic bed and catalyst container, d) a central exchanger (in at least one part of the beds) coaxial with the length of the converter; e) an internal cylindrical wall for the collection of the gas distributed in the external part of the central exchanger tubes; f) a connection and support system located at the ends or extremities of the external solid wall such as to permit the stacking of the single modular cartridges which form the internal cartridge.

The single exchanger located within the beds has its ends or extremities flanged between each other.

The complexity of this system induces the following:

1) even though the single modular cartridges are simply superposed one on each other, they can dissassembled among themselves by simply disconnecting the flanged coupling between the flange at the extremity of the central exchanger;

2) access to connection flanges of the central exchangers is possible only after having emptied the upper bed of all of the catalyst, and by manholes that are located on the bottom of the bed itself;

3) expansion compensators are required in the connection collectors of the exchangers in order to balance the thrusts due to differential expansion of the various parts of the modular cartridges.

This design involves problematic access to the catalytic beds for the removal of the catalyst and the assembly of the cartridge itself (difficulty in installing and removing the catalyst and for the maintenance of the cartridge). In addition, the external wall of the cartridge is contacted by at least one part of the fresh feed gas. This cartridge is not being of one piece, but rather is made of cylindrical sections superposed as described above. Thus, they are susceptible to disalignments due to thermal expansion during use, resulting in imperfect sealing of the coupling of various sections, which may jeopardize the correct functioning and the converter yield (gas bypass).

The Applicant has already proposed a solution that eliminated most of these inconveniences. In Swiss Patent Application 00728/87-5 (see FIG. 2), a cartridge for quench-type converters is described wherein:

a) an external wall of the airspace forming cartridge (with the shell) is a single piece substantially along the axial length of the converter;

b) an external wall forming the beds is completely separate and has no connection whatsoever with the airspace forming wall and is instead made of detached modules each one being delimited in at least one catalytic bed, each module leaning of the module below it; the control of the temperature is, however, carried out here by means of "quench" with fresh gas.

SUMMARY OF THE INVENTION

In the continuation of their research and development studies, the Applicants have now surprisingly resolved the problem of obtaining cartridge for synthesis converters with temperature control between the beds by means of an direct exchange with exchangers, with at least two catalytic beds of axial-radial or radial type and at least one central exchanger for the temperature control between the catalytic beds. According to the invention, the catalytic basket bottoms have means for being coupled and for supported by protruding rings from an internal face of a single body that extends along almost the entire height of the converter and is closest to the external wall of the cartridges-baskets.

In one embodiment of the invention, a complex cartridge comprises:

a) an airspace forming external wall (with the shell) in a single body that extends substantially along the entire axial length of the converter, provided on the internal surface with rings for supporting modular catalyst containing baskets; said external wall is not foreseen for converters that run at lower pressure, in which case the supporting rings are fixed directly to the internal surface of the converter shell the complex cartridge comprises:

an external wall permeable to gas for distributing the gas in the catalytic bed and for containing the catalyst;

a closed bottom provided on the external edge with an unflanged tightness coupling for engaging the supporting ring of the airspace forming wall, said bottom being preferably of a convex shape;

in at least a part of the beds, one central exchanger connected with the exchanger below it by means of an unflanged sealing preferably a labyrinth seal;

in at least one of the beds, a diaphragm arranged on the inside of the internal gas distribution collector for the distribution of gas on the external surface of the central exchanger;

an upper cover or solid wall in the beds with radial gas distribution (inexistant in the beds with axial-radial gas distribution); gas flow in the catalytic beds is distributed from the outside to the inside; and b) modular catalyst containing baskets, each basket being made of:

an external wall permeable to gas for distributing the gas in the catalytic bed and for containing the catalyst;

a closed bottom having an unflanged tightness coupling on an external bottom thereof for engaging the supporting ring of the wall (airspace forming wall or eternal shell), said bottom being preferably of a convex shape;

in at least a part of the beds, a central exchanger connected with a exchanger below it by means of unflanged sealing, preferably a labyrinth seal;

in at least a part of the beds, a diaphragm arranged on the inside of the internal gas distribution collector for distribution of the gas on the external surface of the central exchanger;

an upper cover or solid wall for the beds having radial gas distribution (inexistant in the beds with axial-radial gas distribution);

gas flow in the catalytic beds is distributed from the outside to the inside.

The cartridge presents, with respect to the state of the art, the following advantages:

1) the cartridge is now made of modular cartridges with catalyst (at least 2) completely independent and therefore easily extractable from the external wall of the airspace forming cartridge;

2) easy access to the single catalytic beds is assured by easy dismantling and reassembly of the single cartridge with catalyst;

3) there are no strains due to the diverse thermal expansions of the various parts of the cartridge;

4) perfect sealing of the coupling system (without a flange) with the supporting ring is now guaranteed by the lack of strains due to thermal expansions and by the fact that the airspace forming external wall of the cartridge is a single piece;

5) the convex bottom of the modular cartridge with catalyst increases the volume of the catalyst installable in the bed and therefore the utilization efficiency of the volume on the inside of the shell:

6) the labyrinth seal on the connection collector between the exchangers of the modular cartridges minimum gas flow (lower than 1%) of the total amount of supplies a better coupling guarantee with respect to the flanged couplings, without influencing in any way the high functioning yield of the converter.

BRIEF DESCRIPTION OF THE DRAWINGS

The various aspects and advantages of the invention appear more clearly from the description of the not-limitative embodiments represented in the drawings in which.

DETAILED DESCRIPTION OF THE PREFERRED EMBODIMENT

Figure 1:
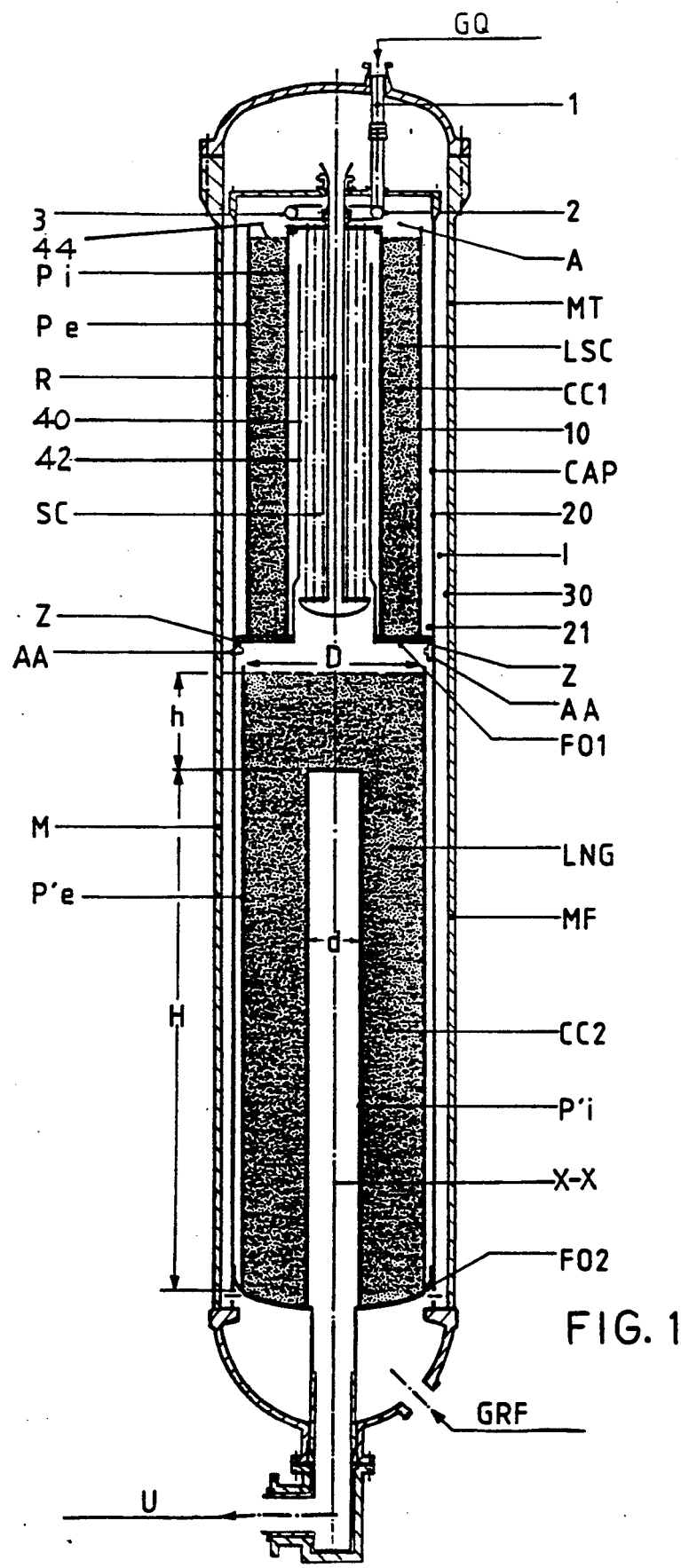
FIGS. 1 to 5 are schematic longitudinal sections with bottom which contains the of converters according to the invention.
Figure 2:
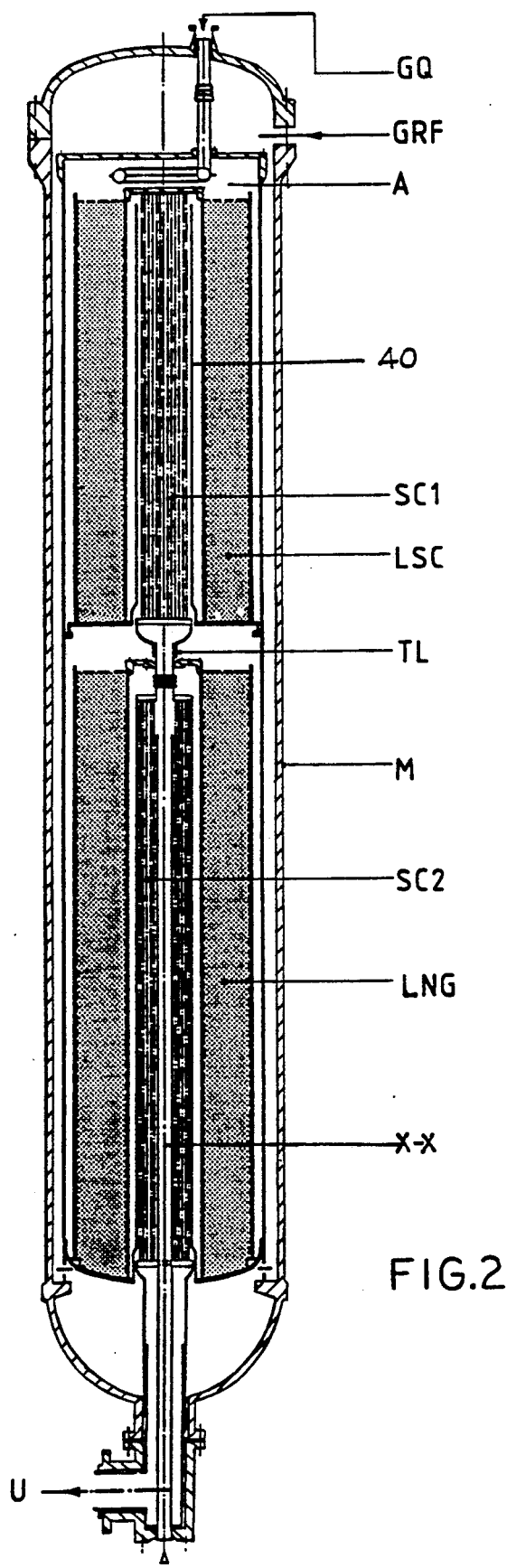
Figure 3:
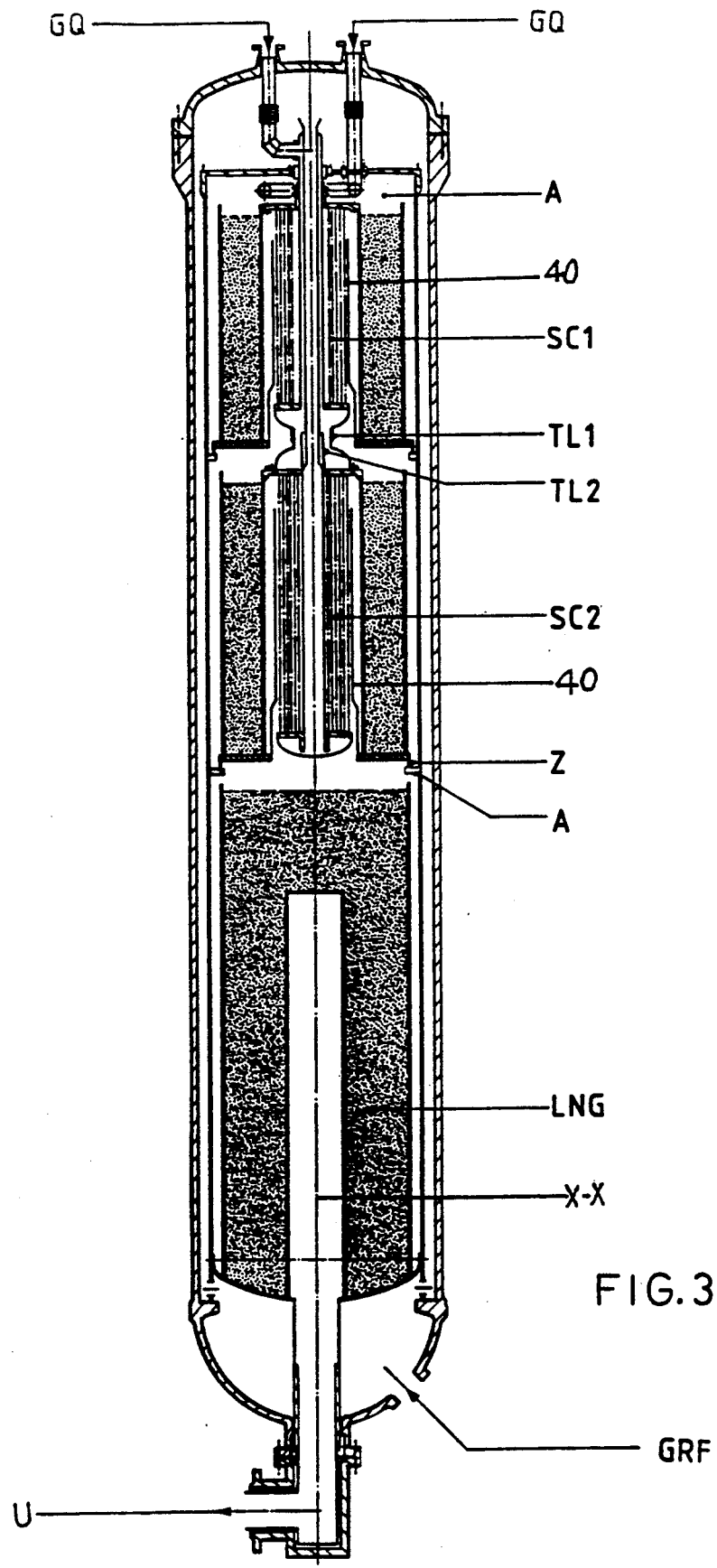
Figure 4:
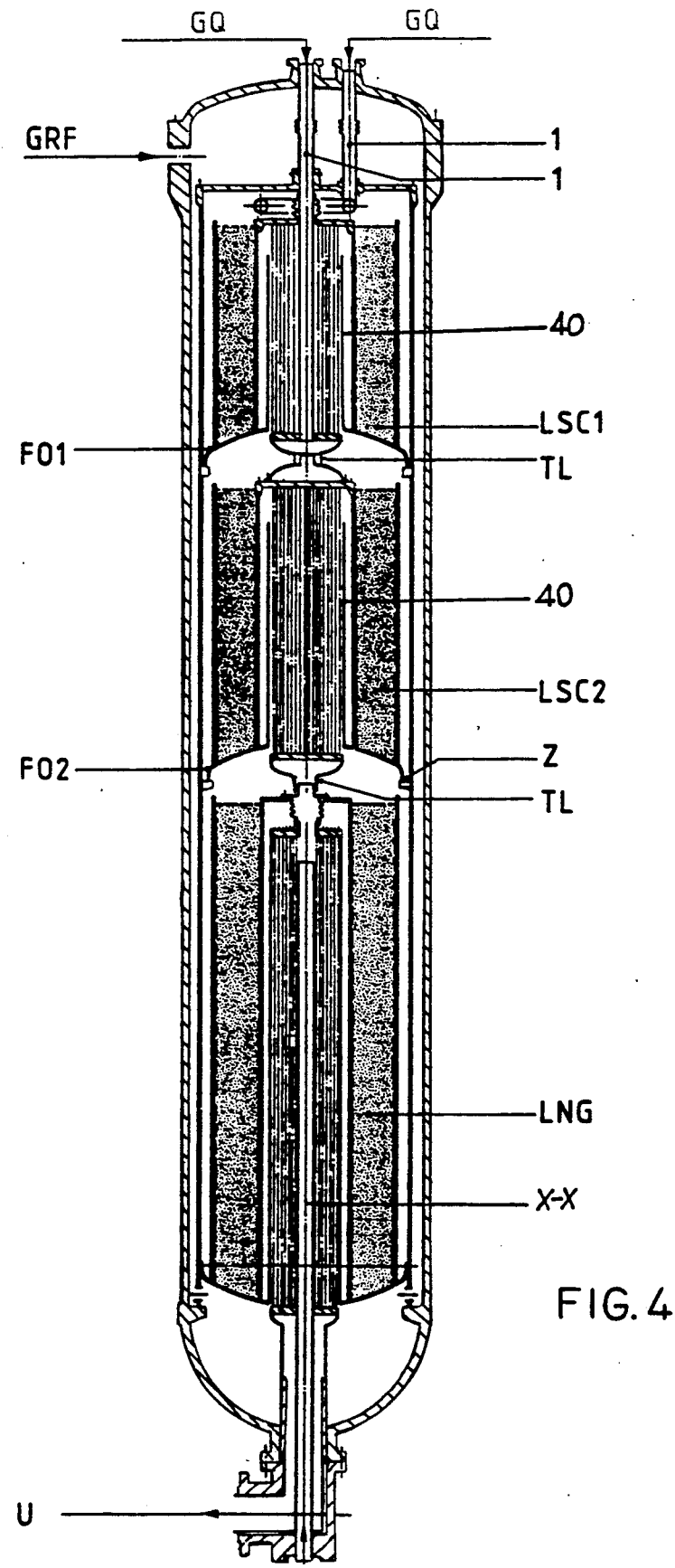

M indicates a shell resistant to pressure with a top portion (MT), a bottom portion (MF) an inner surface 30 and a center line X—X. According to an aspect of the invention, a supporting cartridge (CAP) in a single piece, extends substantially along the entire length of the converter (R), forms with its external face (20) the airspace (I) and presents on its internal face (21) means of support (Z—Z) for the bottoms (FO1 and FO2) of the cartridge-baskets (CC1 and CC2) with catalyst (10). Pi indicate the internal walls and Pe indicates the external walls of a basket, for example CC1 that is open at the top (A) and closed with a bottom (FO1) that is flat for CC1 and convex (FO2) for CC2. Quench gas (GQ) is introduced through a vertical pipe 1 and the openings 2 and 3 in the upper opened zone (A) of CC1 that contains; centrally and practically along its entire height the heat exchanger (SC) in FIG. 1 and (SC1) and (SC2) in FIG. 2 (for example, a type already described in preceding patents by the Applicant). TL, TL1 and TL2 indicated a coupling between exchanger collectors centrally arranged within the catalyst baskets (see FIGS. 2-5). In FIG. 1 the lower basket (CC2) is also formed by an external wall P'e that has a height (H+h) and a diameter (D), and by an internal wall (P'i) that has an height (H) and a diameter (d). Therefore the second basket has a significant amount of catalyst distributed at the top, of height (h) and diameter(D) and a catalyst volume on the height (H) having however diameter (D−d).

Internal gas distribution collector 40 may be located within the catalyst baskets to collect gas exiting the catalyst bed through permeable internal wall Pi. Collector 40 may include a diaphragm 42 to distribute the gas entering the heat exchanger. An upper cover 44 may be located on the catalyst baskets to cause radial gas flow through the covered basket.

Figure 5:
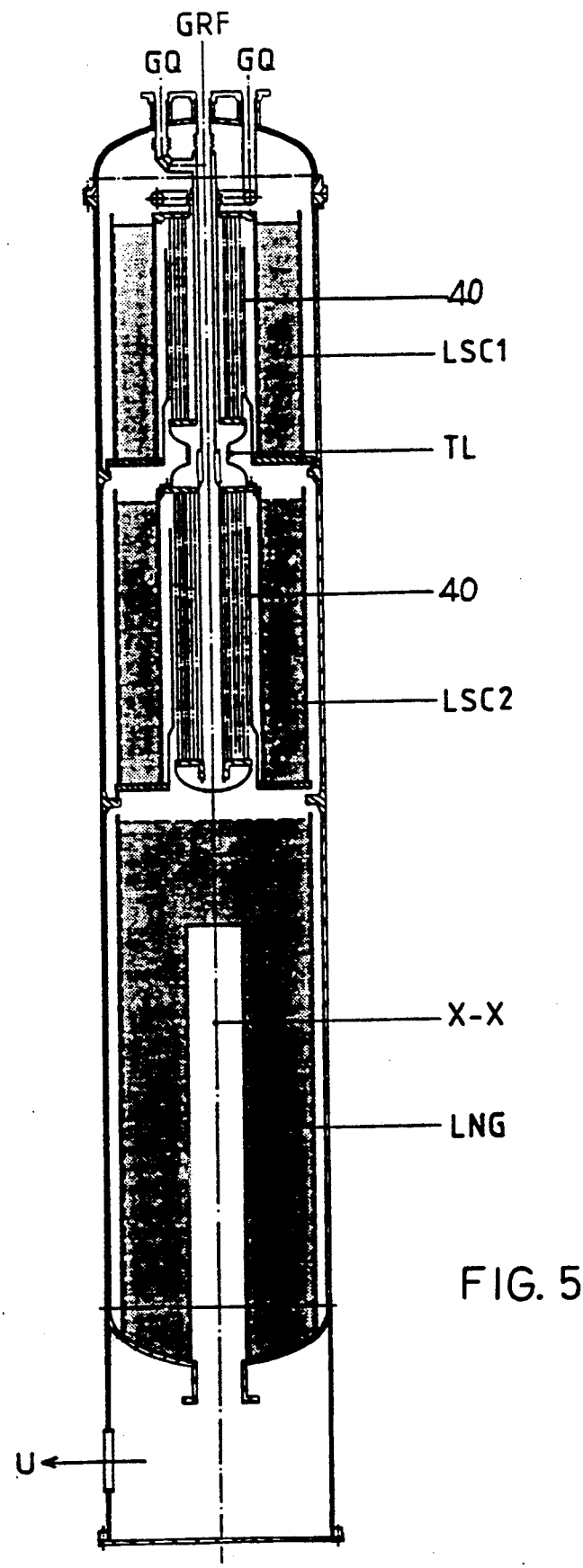
Figure 7:
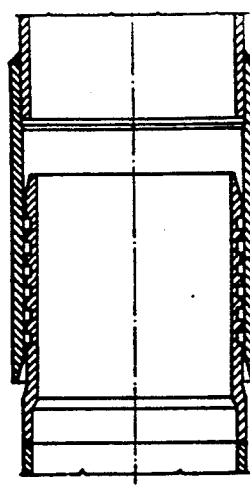
FIG. 7 is a partial view and in longitudinal section of a coupling between exchanger collectors centrally arranged with the catalyst basket.
Figure 6:
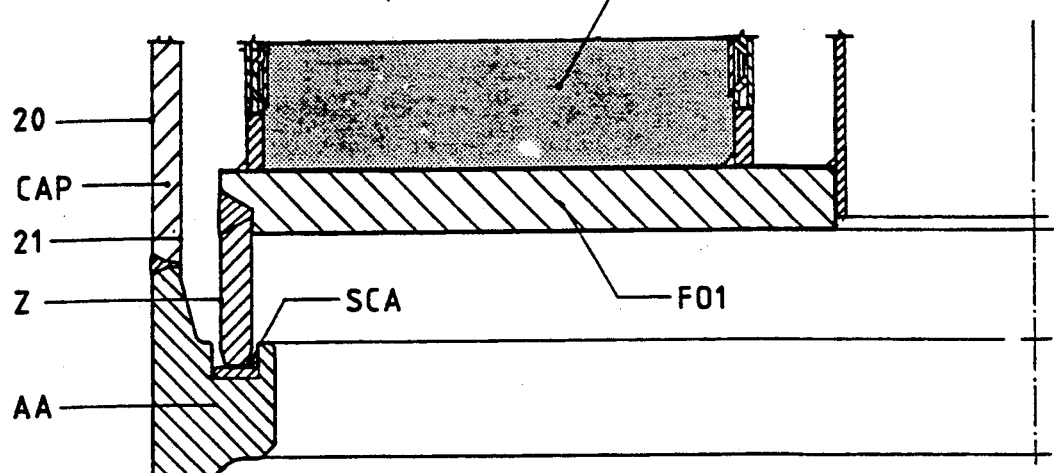
FIGS. 6 and 8 show in partial section on an enlarged scale, a coupling between the flat respectively convex bottom of a cartridge-basket, and the grooved ring protruding from the supporting cartridge.
Figure 8:
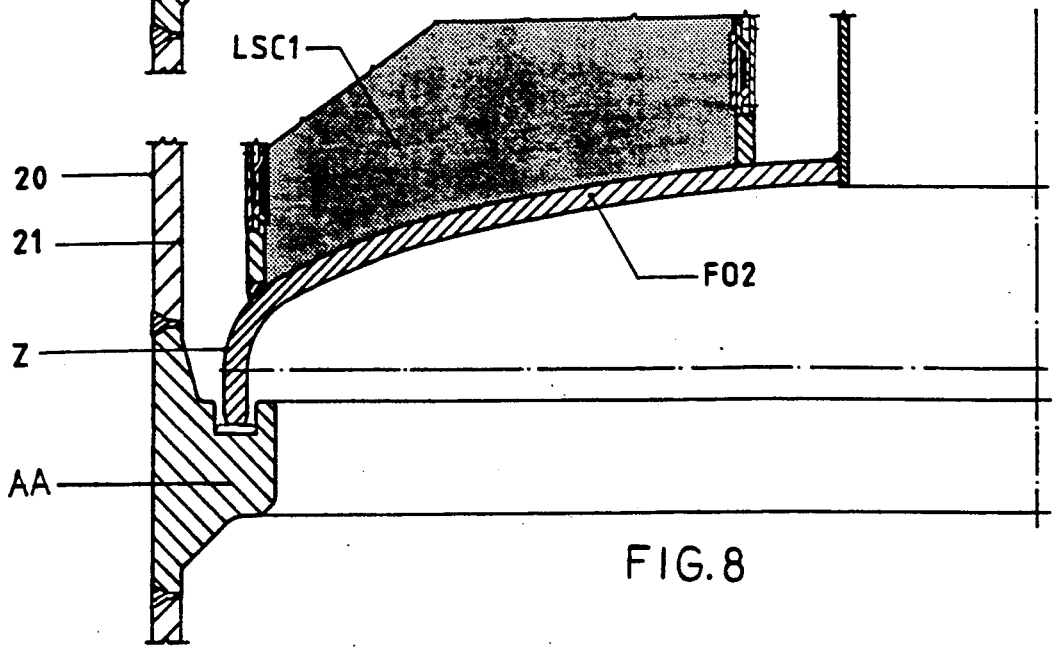

The first catalytic bed with exchanger can be called "bed with exchanger (LSC)", (LSC1 and LSC2 in FIG. 4) the lower one instead, without exchanger, but with catalyst gradient on the heights H and h, can be called "bed without exchanger and with catalyst gradient (LNG)". The bed (LSC) has a flat bottom (FO1) that is supported by downturned sleeves (Z) (FIG. 6) in the protrusions (AA) with grooves (SCA) distributed either along the supporting cartridge (CAP) (FIGS. 1 to 4) and/or along the shell (M) (FIG. 5). GQ indicated the gas quench inlet, GRF indicates the fresh reaction gas and U the outlet of the reaction gas.

We claim:

1. A convertor for heterogenous, catalytic synthesis, comprising:
   1) a one piece, external shell; and
   2) a cartridge located within said shell, said cartridge comprising:

a) a one piece wall for forming an airspace with said shell;
b) a plurality of catalyst baskets located within said airspace-forming wall, each basket containing a catalyst bed and each basket comprising:
   i) a permeable, annular external wall for distributing gas entering said catalyst bed;
   ii) a permeable, annular internal wall located within said external wall for distributing gas exiting said catalyst bed, said external and internal walls defining said catalyst bed;
   iii) a closed bottom having coupling means located on an edge thereof for coupling said baskets to said airspace-forming wall;
c) support means protruding from an internal wall of said airspace forming wall for engaging said coupling means and supporting said catalyst baskets;
d) a heat exchanger centrally located within at least part of one of said baskets;
e) an internal gas distribution collector located within at least one of said catalyst baskets for collecting gas exiting said catalyst bed through said permeable internal wall;
f) a diaphragm located in said collector and associated with said heat exchanger for distributing gas entering said heat exchanger; and
g) a second heat exchanger located within one of said plurality of catalyst baskets positioned below said catalyst basket containing at least part of said centrally located heat exchanger, said heat exchangers being connected by unflanged sealing means.

2. The converter of claim 1, further comprising an upper cover located on at least one of said catalyst baskets for causing radial gas flow through said covered basket.

3. The converter of claim 1, wherein said closed bottom of at least one catalyst basket is convex shaped.

4. The converter of claim 1, wherein said unflanged sealing means comprises a labyrinth seal.

5. The converter of claim 1, wherein said coupling means comprises a tongue and said support means comprises a groove for engaging said tongue.

* * * * *